US008253555B2

(12) United States Patent
Stevenson et al.

(10) Patent No.: US 8,253,555 B2
(45) Date of Patent: *Aug. 28, 2012

(54) MINIATURE HERMETICALLY SEALED RFID MICROELECTRONIC CHIP CONNECTED TO A BIOCOMPATIBLE RFID ANTENNA FOR USE IN CONJUNCTION WITH AN AIMD

(75) Inventors: Robert A. Stevenson, Canyon Country, CA (US); Christine A. Frysz, Orchard Park, NY (US); Scott W. Kelley, Canyon Country, CA (US); Geddes Frank Owen Tyers, Vancouver (CA)

(73) Assignee: Greatbatch Ltd., Clarence, NY (US)

(*) Notice: Subject to any disclaimer, the term of this patent is extended or adjusted under 35 U.S.C. 154(b) by 324 days.

This patent is subject to a terminal disclaimer.

(21) Appl. No.: 12/566,223

(22) Filed: Sep. 24, 2009

(65) Prior Publication Data

US 2010/0060431 A1 Mar. 11, 2010

Related U.S. Application Data

(63) Continuation-in-part of application No. 11/307,145, filed on Jan. 25, 2006, now Pat. No. 7,916,013.

(51) Int. Cl.
*G08B 1/08* (2006.01)
*G08B 23/00* (2006.01)
*A61B 5/00* (2006.01)
*H01Q 1/00* (2006.01)

(52) U.S. Cl. ............. 340/539.12; 340/572.1; 340/573.1; 600/300; 600/301; 128/903; 343/720; 343/873

(58) Field of Classification Search ............. 340/539.12, 340/572.1
See application file for complete search history.

(56) References Cited

U.S. PATENT DOCUMENTS

| 4,376,441 | A | 3/1983 | Duncan |
| 4,424,551 | A | 1/1984 | Stevenson et al. |
| 4,846,158 | A | 7/1989 | Teranishi |
| 5,333,095 | A | 7/1994 | Stevenson et al. |
| 5,336,158 | A | 8/1994 | Huggins et al. |
| 5,855,609 | A | 1/1999 | Knapp |
| 5,905,627 | A | 5/1999 | Brendel et al. |
| 6,216,038 | B1 | 4/2001 | Hartlaub et al. |

(Continued)

FOREIGN PATENT DOCUMENTS

EP  0 534 782 A1  3/1983

(Continued)

OTHER PUBLICATIONS

Wesley J. Clement and Bob Stevenson; Lead Loop Area Measurement of Implantable Pulse Generators and Cardioverter/Defibrillators for Determination of Susceptibility to Radiated Electromagnetic Interference; Heart Rhythm 2005; May 5, 2005; Abstract: 05-AB-2928-HRS, New Orleans, LA.

*Primary Examiner* — Donnie Crosland
(74) *Attorney, Agent, or Firm* — Michael F. Scalise

(57) ABSTRACT

A non-hermetically sealed and biocompatible multi-turn RFID loop antenna is electrically connected to a RFID chip which is enclosed within its own hermetically sealed miniature container. The hermetic seal can be very small and the loop antenna can be relatively large, wherein the entire package is both highly reliable, resistant to body fluids and completely biocompatible. The RFID structure can be implanted in a patient and later communicate with an RFID interrogator to provide information relating to the patient and/or implantable medical devices.

38 Claims, 10 Drawing Sheets

U.S. PATENT DOCUMENTS

| | | |
|---|---|---|
| 6,259,937 B1 | 7/2001 | Schulman et al. |
| 6,275,369 B1 | 8/2001 | Stevenson et al. |
| 6,342,839 B1 | 1/2002 | Curkendall et al. |
| 6,375,780 B1 | 4/2002 | Tuttle et al. |
| 6,566,978 B2 | 5/2003 | Stevenson et al. |
| 6,735,479 B2 | 5/2004 | Fabian et al. |
| 6,765,779 B2 | 7/2004 | Stevenson et al. |
| 6,957,107 B2 | 10/2005 | Rogers et al. |
| 7,017,822 B2 | 3/2006 | Aisenbrey |
| 7,240,833 B2 | 7/2007 | Zarembo |
| 7,333,013 B2 | 2/2008 | Berger |
| 7,479,108 B2 | 1/2009 | Rini et al. |
| 2002/0151770 A1 | 10/2002 | Noll et al. |
| 2008/0048855 A1 | 2/2008 | Berger |
| 2008/0065181 A1 | 3/2008 | Stevenson |

FOREIGN PATENT DOCUMENTS

| | | |
|---|---|---|
| EP | 0 619 101 A1 | 10/1994 |
| WO | WO 96/11722 | 4/1996 |

MINIATURE HERMETICALLY SEALED RFID MICROELECTRONIC CHIP CONNECTED TO A BIOCOMPATIBLE RFID ANTENNA FOR USE IN CONJUNCTION WITH AN AIMD

This application is a CIP of Ser. No. 11/307,145, filed Jan. 25, 2006, now U.S. Pat. No. 7,916,013.

BACKGROUND OF THE INVENTION

This invention relates generally to methods of identifying implanted medical devices. More specifically, this invention relates to implantable and biocompatible radio frequency identification (RFID) tags and associated antennas which may be used with medical devices or for general personal identification purposes.

There are known in the art various methods for identifying implanted medical devices. One such method is the use of X-ray identification tags encapsulated within header blocks of pacemakers or implantable cardioverter defibrillators (ICD). Such X-ray identification tags can be read on an X-ray of the implanted device and provide information to the physician. The information so provided is limited due to space and typically includes only the manufacturer and model number of the implanted device.

It would be beneficial if physicians were able to obtain additional information about an implanted device and/or a patient from an implanted identification tag. Such beneficial information includes, in addition to the manufacturer and model number of the device, the serial number of the device, the treating physician's name and contact information and, if authorized by the patient, the patient's name, contact information, medical condition and treatment, and other relevant information.

Currently, most active implantable medical device (AIMD) patients carry some sort of identification. This could be in the form of a card carried in the wallet or an ID bracelet indicating, for example, that they are a pacemaker wearer of a certain model and serial number. However, such forms of identification are often not reliable. It is quite common for an elderly patient to be presented at the emergency room (ER) of a hospital without their wallet and without wearing any type of a bracelet. In addition, there have been a number of situations where the patient (due to dementia or Alzheimer's, etc.) cannot clearly state that he or she even has a pacemaker.

Oftentimes the ER physician will palpitate the patient's chest and feel that there is an implanted device present. If the patient is comatose, has low blood pressure, or is in another form of cardiac distress, this presents a serious dilemma for the ER. At this moment in time, all that the ER knows is that the patient has some sort of an AIMD implant in his or her chest. It could be a pacemaker, a cardioverter defibrillator, or even a vagus nerve stimulator or deep brain stimulator.

What happens next is both laborious and time consuming. The ER physician will have various manufacturers' internal programmers transported from the hospital cardiology laboratory down to the ER. ER personnel will then try to interrogate the implantable medical device to see if they can determine what it is. For example, they might first try to use a Medtronic programmer to see if it is a Medtronic pacemaker. Then they might try a St. Jude, a Guidant, an ELA, a Biotronik or one of a number of other programmers that are present. If none of those programmers work, then the ER physician has to consider that it may be a neurostimulator and perhaps go get a Cyberonics or Neuropace programmer.

It would be a great advantage and potentially lifesaving if the ER physician could very quickly identify the type of implant and model number. In certain cases, for example, with a pacemaker patient who is in cardiac distress, with an external programmer they could boost the pacemaker output voltage to properly recapture the heart, obtain a regular sinus rhythm and stabilize blood pressure. All of the lost time running around to find the right programmer, however, generally precludes this. Accordingly, there is a need for a way to rapidly identify the type and model number of an active implantable medical device so that the proper external programmer for it can be rapidly identified and obtained.

It is also important to note that lead wire systems generally remain in the human body much longer than the active implantable medical device itself. For example, in the case of a cardiac pacemaker, the cardiac pacemaker batteries tend to last for 5 to 7 years. It is a very difficult surgical procedure to actually remove leads from the heart once they are implanted. This is because the distal TIP and other areas of the leads tend to become embedded and overgrown by tissues. It often takes very complex surgical procedures, including lasers or even open heart surgery, to remove such lead wire systems. When a pacemaker is replaced, the pectoral pocket is simply reopened and a new pacemaker is plugged into the existing leads. However, it is also quite common for leads to fail for various reasons. They could fail due to breakdown of electrical insulation or they could migrate to an improper position within the heart. In this case, the physician normally snips the leads off and abandons them and then installs new leads in parallel with the old abandoned leads.

Abandoned leads can be quite a problem during certain medical diagnostic procedures, such as MRI. It has been demonstrated in the literature that such leads can greatly overheat due to the powerful magnetic fields induced during MRI. Accordingly, it is important that there be a way of identifying abandoned leads and the lead type. Also, there is a need to identify such abandoned leads to an Emergency Room physician or other medical practitioner who may contemplate performing a medical diagnostic procedure on the patient such as MRI. This is in addition to the need to also identify the make and model number of the active implantable medical device.

It is also important to note that certain lead systems are evolving to be compatible with a specific type of medical diagnostic procedure. For example, MRI systems vary in static field strength from 0.5 Tesla all the way above 10 Tesla. A very popular MRI system, for example, operates at 3 Tesla and has a pulse RF frequency of 128 MHz. There are specific certain lead systems that are evolving in the marketplace that would be compatible with only this type of MRI system. In other words, it would be dangerous for a patient with a lead wire designed for 3 Tesla to be exposed to a 1.5 Tesla system. Thus, there is also a need to identify such lead systems to Emergency Room and other medical personnel when necessary. For example, a patient that has a lead system that has been specifically designed for use with a 3 Tesla MRI system may have several pacemaker replacements over the years.

It is already well known in the prior art that RFID tag implants can be used for animals, for example, for pet tracking. It is also used in the livestock industry. For example, RFID tags can be placed in cattle to identify them and track certain information. An injectable RFID tag for humans has also been developed. However, none of the current RFID tags have been designed to have long term reliability, hermaticity, and biocompatibility within the body fluid environment.

In the prior art, RFID tags have been encapsulated in plastic or placed in a plastic or glass tube with an epoxy infill. However, as will be discussed more fully below, none of these materials provide a truly hermetic seal against body fluids.

With reference now to FIGS. 1 and 2, prior art RFID chips 12 typically involve a small substrate 14 on which a microelectronic chip 16 is placed along with an embedded or printed antenna 18. These antennas can be Wheeler spirals, rectangles, dipoles, solenoids or other shapes. The read range of such antennas, particularly for low frequency (LF) and high frequency (HF) readers tends to be very short. That is, the RFID reader has to be in very close proximity to the RFID chip. In order to extend the read range, a larger loop style antenna 18 involving multiple turns, as illustrated in FIG. 2, is typically used. These involve very fine wire, multiple turns of copper, which are then soldered to the RFID chip. Obviously, neither copper nor solder joints are biocompatible or even reliable for human body implants. When exposed to body fluids, copper causes corrosion problems as well the tin and lead that is typically used in solders. These materials, when leached out can even become toxic to the human body.

One approach would be to hermetically seal the RFID chip and its complete loop antenna. However, when one fully contemplates hermetically sealing an RFID chip with a very large multi-turn loop antenna, one realizes that such an approach becomes entirely impractical. The hermetic seal package would simply be too large to be effectively associated with a medical implant.

Accordingly, there is a need for an improved medical identification tag that can store additional information about an implanted device and/or a patient, without unduly increasing the size of the identification tag or jeopardizing the operation of the implanted device or the health of the patient. The present invention meets these needs by providing an RFID tag that can be enclosed within an AIMD or introduced into a patient's body adjacent to an AIMD or lead wires. The RFID tag of the present invention is capable of storing information about the medical device, the physician, and the patient, as described above.

SUMMARY OF THE INVENTION

In general, the present invention is directed to a system for identifying implants within a patient, comprising an implantable medical device, a radio frequency identification (RFID) tag having a hermetically sealed chip and biocompatible antenna and being associated with the implantable medical device, the RFID tag containing information relating to the patient and/or the implantable medical device, and an interrogator capable of communicating with the RFID tag.

Such implantable medical devices may include active implantable medical devices (AIMD) such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion, or a prosthetic device and component parts thereof, including lead wires or abandoned lead wires. The active implantable medical device may include a non-metallic header or connector block in which the RFID tag is implanted. The RFID tag may be disposed within the non-hermetically sealed portion, such as the header block, of the medical device. In one embodiment, the RFID chip includes information pertaining to the medical device.

More particularly, the present invention resides in a relatively large multi-turn RFID loop antenna, which is biocompatible and is electrically and mechanically connected to an RFID chip which is enclosed within its own hermetically sealed miniature container. Such design allows the hermetic seal to be very small and the loop antenna to be relatively large, wherein the entire package is both highly reliable, resistant to body fluids and completely biocompatible. Moreover, the present invention is adaptable for being molded into the header block, for example, of a cardiac pacemaker. However, the present invention could also be put in a small disk comprised of non-conductive biocompatible material, and literally implanted anywhere in the human body. The biocompatible material may comprise a disk of silicone, epoxy, or a medical grade plastic. In other words, it doesn't have to be directly associated with the implanted medical device. Another application of the present invention is that it could be implanted in a location in the human body, independent of the AIMD, and contain important information about the patient, the patient's medical condition, the patient's medical history or the like.

In a preferred embodiment, the present invention resides in an implantable radio frequency identification (RFID) tag comprising a hermetically sealed biocompatible container. An RFID microelectronics chip is disposed within the container. A biocompatible antenna extends from the RFID microelectronics chip and exteriorly of the container.

The container comprises a housing taken from a group including biocompatible metals and alloys, ceramic, glass, porcelain, sapphire and composites thereof, and specialty polymer composites. The hermetic container has a leak rate of no more than $10^{-7}$ cubic centimeters per second. Typically, the container includes a cap hermetically sealed to the housing. Biocompatible electrical/mechanical connections are made between the antenna and the container or the antenna wires can directly penetrate a hermetic ceramic container and be co-fired with it. In one embodiment, the container includes terminal pins extending therethrough and conductively coupled to the antenna and the RFID microelectronics chip.

In another embodiment, an encapsulant within the housing surrounds at least a portion of the RFID chip. The encapsulant may be comprised of a thermal-setting polymer or a silicone material. A desiccant may also be included within the housing.

A sensor may be conductively coupled to the RFID microelectronics chip. The sensor may be disposed within the container, or exterior to the container.

In another embodiment, the antenna is wound around a ferrite-based core. The ferrite-based core may be comprised of a high temperature sintered ferrite-based material. A biocompatible dielectric material may at least partially coat the ferrite-based material. Such biocompatible dielectric material may comprise parylene, ETFE, PTFE, polyimide, polyurethane or silicone. Preferably, the ferrite-based core is comprised of a ferrite material that will not exhibit permanent remanence after exposure to MRI fields.

Typically, the RFID tag comprises a portion of a system which includes an interrogator for electromagnetically communicating with the RFID chip. A radio frequency of between 132 kHz and 915 MHz is used to communicate with the RFID chip. In a particularly preferred embodiment, the radio frequency used to communicate with the RFID chip is either 125 to 135 kHz (LF) or 13.56 MHz (HF). The RFID chip may be read-only or readable/writeable. As such, the interrogator may be read-only or a reader/writer device. Moreover, the interrogator may be in communication with a computer or a computer network.

These and other aspects of the invention will be apparent to one skilled in the art in light of the following detailed description of the preferred embodiments.

BRIEF DESCRIPTION OF THE DRAWINGS

The accompanying drawings illustrate the invention. In such drawings.

DETAILED DESCRIPTION OF THE PREFERRED EMBODIMENTS

The present invention is directed to a radio frequency identification (RFID) system for use with active implantable medical devices (AIMDs) and an associated RFID tag. Specifically, the RFID system comprises an RFID tag implanted in a patient's body and associated with an implanted AIMD, and an interrogator in communication with the RFID tag. The novel tag comprises a hermetically sealed electronic RFID chip and an external biocompatible antenna.

Figure 1:
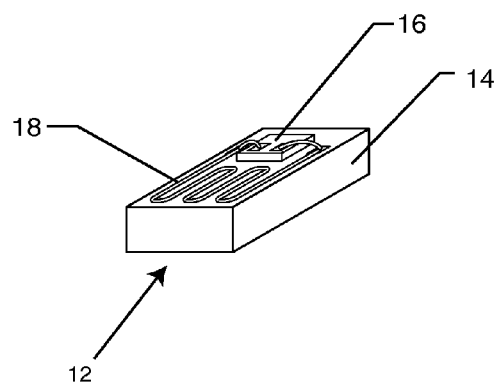
FIG. 1 is an isometric view of a prior art RFID tag.
Figure 2:
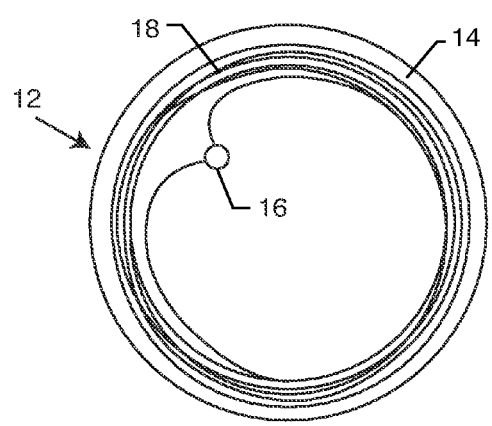
FIG. 2 illustrates a prior art RFID chip and associated antenna.
Figure 3:
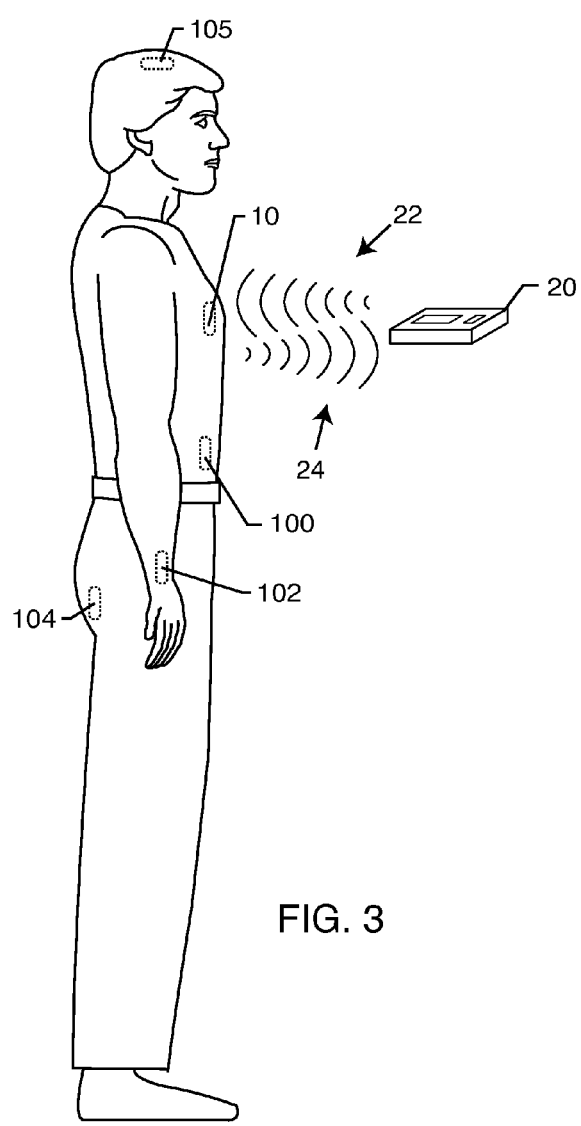
FIG. 3 is a depiction of a patient with an AIMD fitted with an RFID tag of the present invention and an external interrogator/reader.

FIG. 3 is an outline drawing of an adult male pacemaker patient with an AIMD 10. One potential location for an AIMD 10, shown by a dashed ellipse, which is typical of a right or left pectoral muscle implant. Right and left pectoral muscle implants are typical for a cardiac pacemaker or implantable cardioverter defibrillator (ICD). The right and left pectoral muscle region is chosen due to the easy access to the cephalic or subclavian veins for insertion of lead wires and electrodes down into the heart. The present invention may also find application in AIMDs such as, an implantable defibrillator, a congestive heart failure device, a hearing implant, a cochlear implant, a neurostimulator, a drug pump, a ventricular assist device, a drug pump, a spinal cord stimulator, an implantable sensing system, a deep brain stimulator, an artificial heart, an incontinence device, a vagus nerve stimulator, a bone growth stimulator, a gastric pacemaker, or a prosthetic device. Other locations, such as the abdomen, wrist, buttocks, and skull are shown by dashed ellipses (100, 102, 104 and 105) which could represent an AIMD or a location where the RFID tag of the present invention is situated.

Referring once again to FIG. 3, one can see an RFID interrogator 20, also known as a hand held scanner or reader. The interrogator 20 transmits an electromagnetic field pulse 22 which is intercepted by the antenna 18 that is part of the implanted RFID tag 12. The implanted RFID tag 12 is generally passive. That means that it does not have its own self-contained source of energy such as a battery (although it can). The electromagnetic field 22 that comes from the interrogator 20 resonates with the antenna 18 and RFID chip 16 providing energy for the RFID chip 16 to generate a signal and the antenna 18 to emit a return pulse 24. This pulse 24 is picked up by an antenna 26 in the interrogator 20. The pulse 24 contains digital modulation. As previously described, this digital modulation can contain information such as the model number of the patient's AIMD, the serial number of the AIMD, the manufacturer of the lead wire system, the name of the patient's physician, and contact information for the physician. In addition, if the patient authorizes, the digital pulse can also contain the patient's name, the patient's medical condition, the patient's address and telephone number, and other pertinent information.

Figure 4:
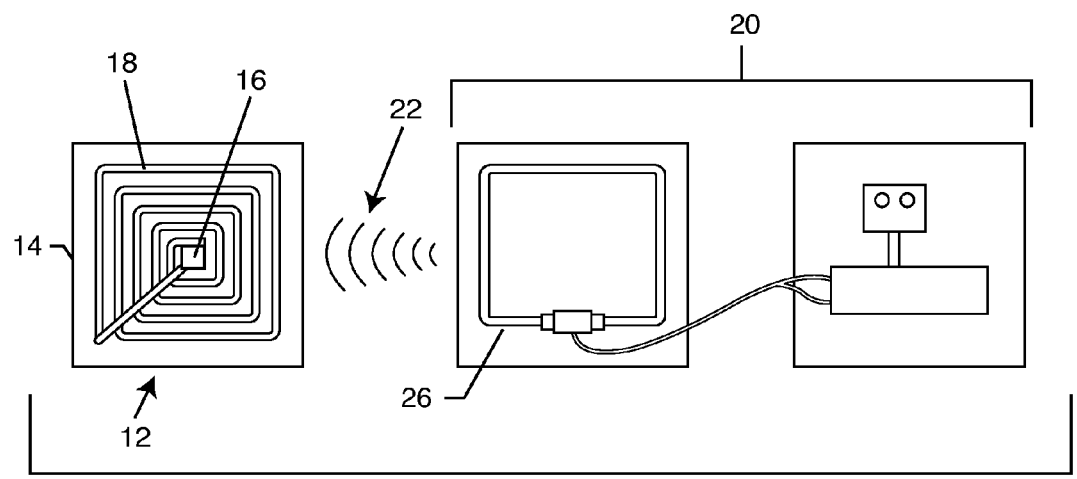
FIG. 4 is a block diagram depicting operation of a system including the RFID tag of the present invention.
Figure 5:
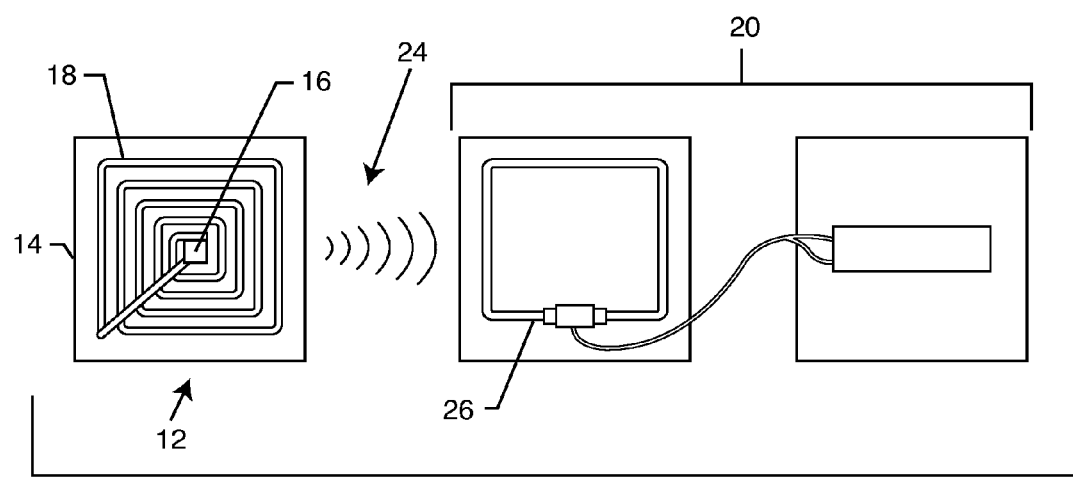
FIG. 5 is a block diagram depicting operations of an alternative system including an RFID tag.

FIGS. 4 and 5 depict block diagrams of the RFID system in operation. As described above, the RFID tag 12 consists of a substrate 14, an RFID chip 16, and an antenna 18. The interrogator 20 with associated antenna 26 discharges electromagnetic energy 22 to the antenna 18 of the RFID tag 12, which powers up the RFID chip 16 and allows it to produce the electromagnetic return signal 24, as shown. The electromagnetic return signal 24 is detected by the interrogator 20 and presented as a digital code sequence. The RFID tag 12 may be read-only (RO) or read/write (RW). With an RW RFID tag 12, a physician may use an external programmer or interrogator 20 to write additional patient information to the RFID tag 12. This additional information may include patient name, patient address, medical condition, and so on. In the case of an RO RFID tag 12, the RFID tag 12 would be installed at the time of AIMD manufacture and would designate manufacturer, model number and other key information. However, an RO RFID tag 12 would not be later programmable and could not include added important information such as patient name, doctor name, patient diagnosis and so forth. The interrogator 20 may comprise programmer or programmer/reader, which would permit direct display of all of the information contained on the RFID tag 12.

Ideally, the medical device manufacturer would have a special RFID reader associated with their manufacturing line. For example, a cardiac pacemaker manufacturer, at the point of final sterilization and packaging, would use a production line barcode reader-RFID writer to read the barcode 178 associated with the production lot traveler or packaging 176 and then this production line RFID writer would write this information to the tag that is embedded in or associated with the pacemaker or other medical device. This would go into an area of permanent memory on the RFID tag. There would also be an area of volatile memory that the doctor could optionally use later to enter information about the patient, the patient's medical condition or even information about the implanting physician all at the time of implant. This would typically be done with informed patient consent. Of course, these principles are applicable to any external or internal medical device. Moreover, the RFID chip associated with the AIMD need not be embedded in the header block within the housing of the AIMD. The RFID tag could also be implanted in other locations within the patient's body even within a special patient ID card.

Figure 6:
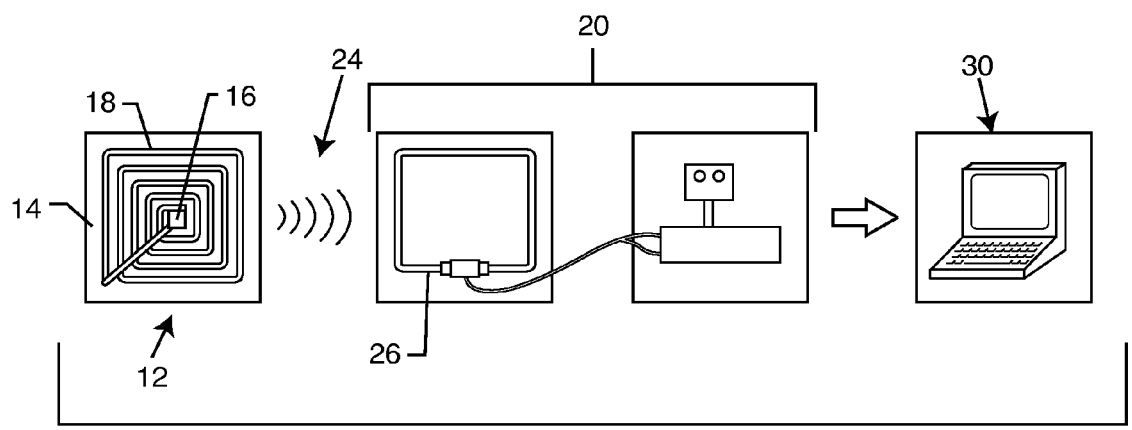
FIG. 6 is a block diagram depicting operation of another alternative system including an RFID tag.

FIG. 6 illustrates a very similar system as previously described in FIGS. 4 and 5 except that the interrogator 20 is designed to be integrated with a computer system 30 which may be linked to the worldwide web. In this case, a unique digital number transmitted by the RFID tag 12 may be entered into the computer system 30. The computer system 30 maintains a database of important information that is all keyed to the digital information transmitted by the RFID tag 12. In this way, the physician or emergency room personnel may obtain the digital code from the RFID tag 12 which enters automatically (or manually) into the computer system 30 to immediately get a download, including all of the information required as to the model and serial number of the AIMD, lead wire system, patient and physician information, and patient history when available. The RFID tag could also access the new American College of Cardiology National Cardiovascular Data Registry (ACC-NCDR). ACC-NCDR is a comprehensive cardiac and date repository for three national registries: the CathPCI Registry, the CarotidStent Registry, and the ICD Registry. The ICD Registry was developed in partnership with the Heart Rhythm Society and is designed for participation by hospitals. It collects detailed information on ICD implantations and has as one of its missions helping hospitals meet regulatory requirements and Medicare requirements.

Figure 7:
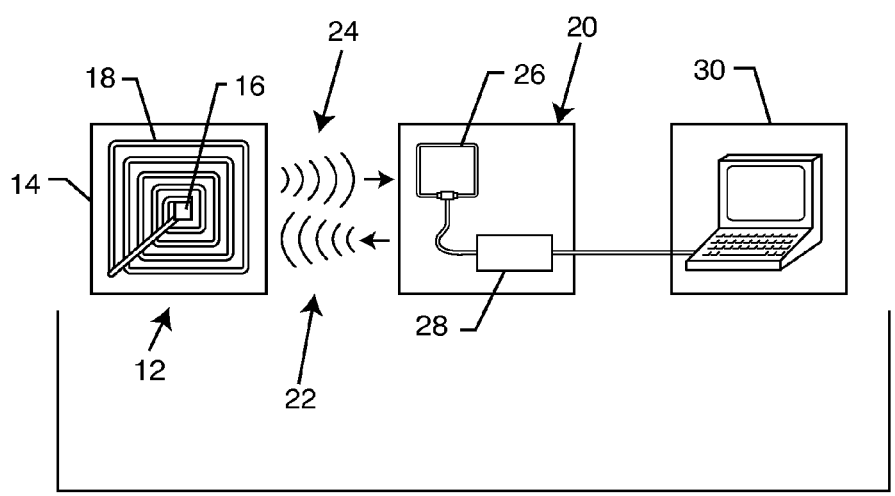
FIG. 7 is a block diagram depicting operation of yet another alternative system including an RFID tag of the present invention.

FIG. 7 illustrates a system very similar to that described in FIG. 6 except that the output of the interrogator 20 would go to an antenna and processor 28 which are designed to be linked directly to a laptop computer 30. This could be done by USB or equivalent cable interface network. The laptop computer 30 may contain a full database by model numbers and serial numbers of medical implantable devices. A drawback to this type of system is that it would be very difficult to keep updated with current patient and physician information.

RFID standards are evolving worldwide at various frequencies generally between 125 kHz and 915 MHz. For example, a 915 MHz protocol is generally evolving to be used for retail goods and inventory control. However, due to the high frequency, the 915 MHz protocols are not very useful for human implants. The reason for this is that humans are largely water and 915 MHz fields are greatly affected by the presence of water. The preferred embodiment is another RFID protocol which operates at 13.56 MHz which is ideal for an implantable RFID tag. The 13.56 MHz lower frequency will readily penetrate and communicate with the tag instead of reflecting off of the skin surface or being absorbed. There are other lower frequency RFID systems, for example, in the 125 to 135 kHz range which would also be ideal.

Figure 8:
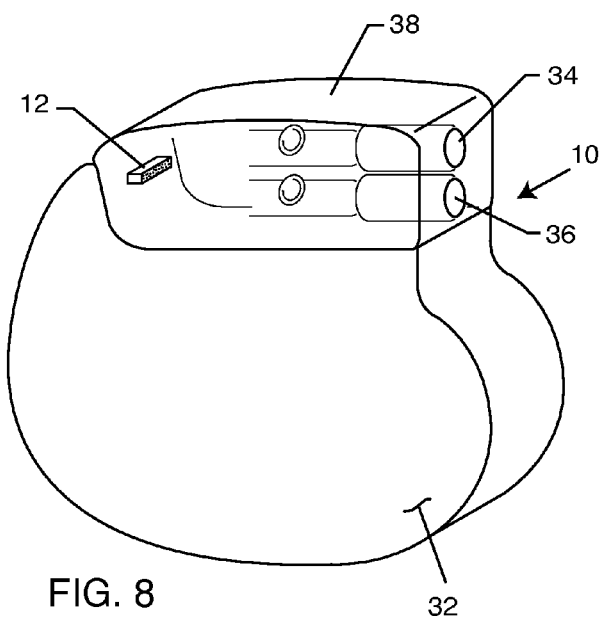
FIG. 8 is an isometric view of a typical AIMD fitted with an enclosed RFID tag.

FIG. 8 is an isometric view of a typical AIMD 10, such as a cardiac pacemaker. Cardiac pacemakers typically have a metallic housing 32 which can be of titanium, stainless steel or the like. This metallic housing 32 is laser welded shut and generally contains a hermetic feedthrough terminal for passage of lead wires into the interior of the metallic housing 32. Said hermetic feedthrough terminals are well known in the art and are generally laser welded into the metallic housing 32 of the implantable medical device. The cardiac leads (not shown) are generally routed to connectors 34, 36. The connectors 34, 36 provide a convenient location to plug in the leads which are routed to the heart for pacing and biologic sensing. The connector assembly 34 and 36 is generally encapsulated within a molded non-metallic, i.e., plastic or ceramic, header block 38, as shown. Usually, this header block 38 is of clear casting materials which are well known in the art. Opaque thermal setting or chemically setting materials may also be used.

FIG. 8 shows a non-hermetically sealed RFID tag 12 which is encapsulated within the molded header block 38 of an AIMD such as a cardiac pacemaker. Such molded header blocks are common in the industry and are designated by ISO Standards IS-1, DF-1 or IS-4 or the equivalent. Referring to FIG. 8 one can see that this header block material is a solid encapsulated material such as an epoxy, thermal setting polymer or the like. In general such materials are not considered truly hermetic and will have leak rates varying from $10^{-5}$ to $10^{-6}$ cubic centimeters per second. Accordingly, if such active implantable medical device 10 as shown in FIG. 8 were implanted for long periods of time, then body fluids would eventually, due to the bulk permeability of the header block 38 material reach the electronic circuits of the RFID tag 12. Body fluids are comprised primarily of water and dissolved salts including sodium, chlorine, potassium, calcium and the like. These are ionic and if they reach the surfaces of the RFID tag 12 it will readily short it out. There is a worse problem than the RFID tag shorting out. That is, the RFID tag itself may contain materials that are not biocompatible and may be toxic to body tissues. For example, when the RFID microchip itself is viewed under high magnification, one can see that there are hundreds, if not thousands of electronic circuit connections, which can contain tin, cadmium or even lead.

Prior art RFID chips that are used for both animal and sometimes for human implant have a serious deficiency in that they are not truly hermetically sealed. These devices often use a cylindrical glass cup which is filled with epoxy or other type polymer materials such as silicone or the like. A deficiency with such seals as mentioned above is, that over long periods of time, moisture will slowly penetrate and reach sensitive electronic circuits. When moisture reaches electronic circuits under low bias voltage conditions, dendrites and tin whiskers can form thereby shorting out or reducing insulation resistancy to electronic components. There is another problem of great concern and that is not all of the materials that are used within the RFID chip itself (for example within the ASIC electronics) are biocompatible. Therefore, moisture intrusion over long periods of time can lead to issues with toxicity to surrounding tissues as these non-biocompatible materials leach out. Accordingly, it is the preferred embodiment of the present invention that the RFID chip be completely hermetically sealed with a minimum leak rate of $1 \times 10^{-7}$ cubic centimeters per second. As used herein "hermetically sealed" means a leak rate of $10^{-7}$ cubic centimeters per second or slower. In fact, in the preferred embodiment a maximum leak rate of at most $1 \times 10^{-12}$ cubic centimeters per second is preferred. This is in sharp contrast to prior art polymer fill systems which achieve at most a leak rate of around $1 \times 10^{-5}$ cubic centimeters per second, and are not considered hermetic seals in accordance with the present invention. Thus, in the preferred embodiment as will be described herein, the electronic chip portion of the RFID tag 12 will be hermetically sealed.

The hermetic seal characteristics of the header block assembly 38 depend upon the ability of the molding or plastic materials of the header block 38 to prevent body fluids from penetrating to the RFID tag 12. Penetration of body fluids over time to the RFID tag 12 may cause degradation of insulation, resistance, or short circuits. Accordingly, hermetically encapsulating the RFID tag 12, as will be described below, is the preferred embodiment.

Since the RFID tag 12 microcircuit is generally constructed of materials that are not long term biocompatible and body fluid resistant, it is important to prevent body fluids from reaching the RFID tag microcircuit 12. Even if the RFID tag 12 is embedded deeply within a molded polymer header block 38 as illustrated in FIG. 8, when such a device is implanted into body tissue for many years (cochlear implants may last forty years or longer), moisture can slowly penetrate due to the bulk permeability of the polymer material of the header block 38. In the art, this is known as the leak rate or hermeticity of a device. Generally speaking, adjunct sealants, polymers and the like are not considered truly hermetic. A leak rate of $10^{-7}$ cubic centimeters per second or slower is required to assure that moisture will not penetrate to sensitive electronics over long periods of time. In order to achieve such low leak rates, generally glass seals or gold brazed ceramic seals are required. It is well known that brazed ceramic seals are generally superior to fused or compression glass seals.

The present invention resides in RFID readers and systems in order to interrogate and identify an active implantable medical device. In order for the RFID field to be able to read a tag embedded within the human body, it must generate a very powerful yet relatively low frequency field. As previously described, the preferred embodiment is a 125 to 135 kHz LF or a 13.56 MHz HF RFID tag and reader. Such readers are most effective when held within 10 centimeters of the implant. In general, these are 3 to 6-watt effective radiated power (ERP) devices. In comparison, a cellular telephone which produces a very powerful near field is only a 0.6 to 2-watt ERP device. Thus, the patient with an active implantable medical device is subjected to a very powerful digitally pulsed RFID reader field. Accordingly, it is a feature of the present invention that the AIMD have very robust shielding and filtering against the electromagnetic interference that is being produced by the RFID reader itself. This is in order to assure that the electronics of the AIMD are not subjected to temporary or permanent malfunction. Instances of pacemaker inhibition, microprocessor reset or even permanent damage to device electronics have all been documented in the past due to EMI. Accordingly, there is a need in combination with the present invention for the AIMD to incorporate EMI filters that are particularly robust so it will be resistant to the fields produced by the RFID reader.

Figure 9:
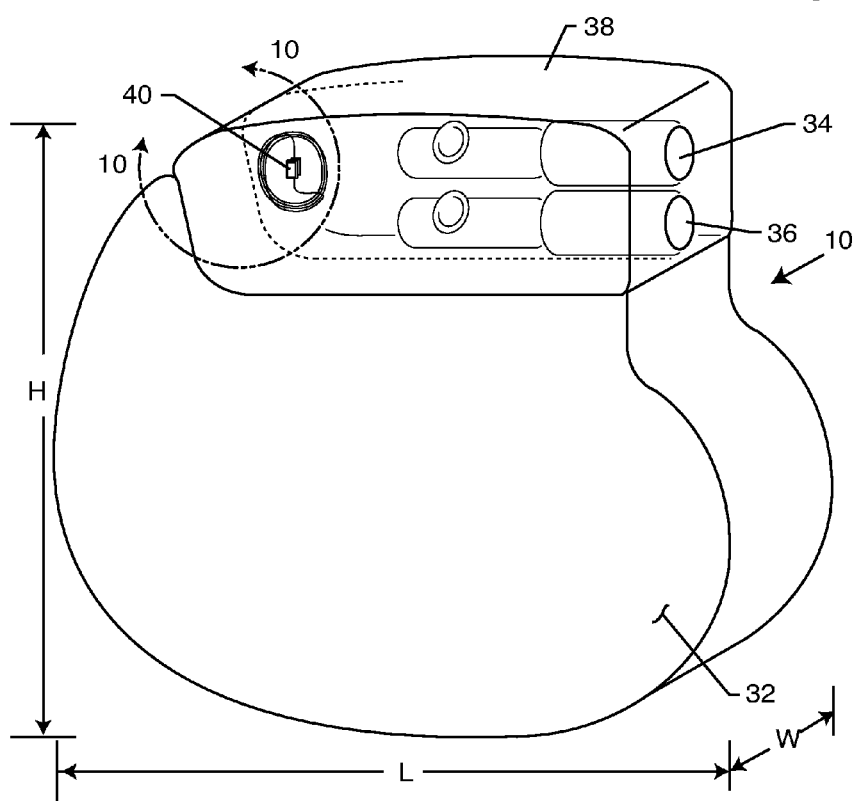
FIG. 9 is an isometric view of a typical AIMD similar to FIG. 8 fitted with an RFID tag disposed within a hermetic enclosure, wherein a biocompatible loop antenna extends outwardly from the hermetic container.

FIG. 9 is very similar to FIG. 8 in that, the plastic header block 38 of an AIMD is shown. In FIG. 8, an RFID tag 40 is shown embedded within the plastic header block. Header blocks and associated connectors are well known in the art. For example, for cardiac pacemakers, they are completely defined by International Standards Organization (ISO) Standards IS-1, DF-1 and IS-4. The reason one would place the RFID tag in the header block is that the header block materials are non-metallic and are therefore transparent to electromagnetic energy from an RFID reader. This is particularly advantageous if the RFID frequency were to be at 13.56 MHz or above. For low frequency RFID tags (LF) that operate typically at 125 to 135 kHz range, the RFID tag could be in the header block or even inside the titanium housing of an AIMD. Obviously, if the RFID chip and its associated antenna were in the hermetically sealed titanium housing 32, as shown in FIG. 9, then the present invention embodying a biocompatible multi-turn loop antenna connected to a hermetically sealed RFID chip would not be required. However, to achieve optimum read range, it's preferable that the RFID chip and its associated antenna not be inside the electromagnetic shielded housing of an AIMD.

Referring back to FIG. 9, one can see that the RFID tag 40 has been embedded in header block 38 and is connected to a multiple-turn antenna 42. Read range is important in the present application. The read range should not be too excessive (for example, several meters) because of the possibility of creating electromagnetic interference (picking up stray tags and so on). However, a read range of approximately 4 inches would be optimal. Most implantable medical devices, such as cardiac pacemakers and implantable cardioverter defibrillators (ICDs) are implanted under the skin. In these cases, the implant depth would only be about 12 millimeters. However, for a person who is morbidly obese, this distance could increase significantly, especially if the implant was placed subpectorally or in a pocket down beneath the breast. In this case, a read range closer to 100 millimeters would be desirable. One might be tempted to place the RFID tag 40, closer to one side of the header block than the other. The problem with this is one cannot rely on the implanting physician to always implant the device with one side up. Furthermore, there is the syndrome that has been well documented in the art as Twiddler's Syndrome. Twiddler's Syndrome involves the pacemaker or other AIMD patient, either consciously or subconsciously, manipulating their implanted device. There have been documented cases that over a period of months or even years, the pacemakers have been twisted or revolved around several times in the pocket to the point where the leads are broken or pulled out. In other more extreme cases, the twiddler can actually flip the pacemaker over. Accordingly, in a preferred embodiment of the present invention, the RFID circular antenna and its associated chip 40 would be implanted parallel to the length and height (L, H) plane of the AIMD and midway or halfway in width W. In this case, it would not really matter which side was up when the physician implanted the device as the distance to the RFID antenna would remain constant. This also solves the issue with Twiddler's Syndrome in that it would not matter, again, which way the pacemaker was oriented.

Figure 10:
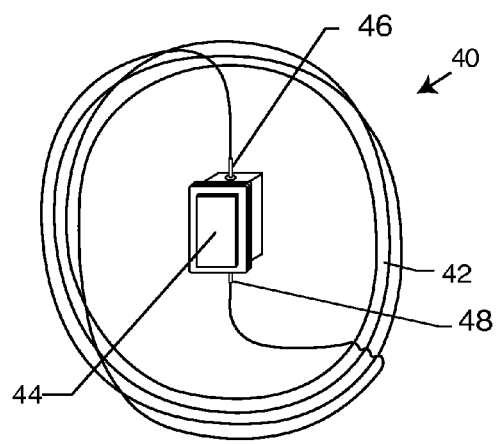
FIG. 10 is an enlarged view of an RFID tag taken of the area indicated by the line 10-10 in FIG. 9.

FIG. 10 is generally taken from line 10-10 from FIG. 9. This shows the multiple turn loop antenna 42 which consists of biocompatible conductive materials, such as titanium, platinum and platinum/iridium alloys, tantalum, niobium, zirconium, hafnium, nitinol, Co—Cr—Ni alloys such as MP35N, Havar®, Elgiloy®, stainless steel, gold and its various alloys, palladium, or any other biocompatible or noble metal. Conductive metal compounds could also be used to form a biocompatible antenna of the present invention and these include: ZrC, ZrN, TiN, NbO, TiC and TaC. In addition, the antenna could be formed on some sort of a substrate with conductive polymers: Polyenthylene Oxide with ionic addition such as NaCl (see U.S. Pat. No. 6,295,474), also, any of the commonly used implantable polymers, such as Polyurethane, Silicone, Polyesters, Polycarbonate, polyethylene, Polyvinyl Chloride, Polyporpylene, Methylacrylate, Paraxylylene. These can all be made conductive by adding a biocompatible particulate filler, such as platinum powder or flake. Another type of conductive biocompatible material, from which an antenna could be made, is pyrolytic carbon.

With reference again to FIG. 10, a hermetically sealed package 44 contains the RFID chip 40. There are biocompatible electrical connections 46 and 48 between the antenna 42 and the hermetic seal assembly terminals 44. These would typically be laser welds or brazes of all biocompatible materials or biocompatible solders or conductive polymers. In other words, no non-biocompatible solder joint or other such non-biocompatible connection would be exposed to body fluids. An alternative would be to use a biocompatible thermally conductive adhesive. Biocompatible metals and alloys that can be used for the electronic network components or component network or the connection materials include all of the metals and alloys of titanium, platinum and platinum iridium alloys, tantalum, niobium, zirconium, Hafnium, nitinol, Co—Cr—Ni alloys such as MP35N, Havar®, Elgiloy®, stainless steel and gold. There are also a number of conductive metal compounds that can be used including ZrC, ZrN, TiN, NbO, TiC, TaC, and Indium Oxide/Indium Tin Oxide (Transparent Conductive Oxides). Commercially available biocompatible electrically conductive epoxies are manufactured by Epoxy Technology, Inc, in Billerica, Mass. For example Epoxy technology EPO-TEK H81 features a biocompatible epoxy which is gold filled (www.epotek.com). The conductive connection materials are typically thermalsetting, brazing, welding or special biocompatible soldering materials. So as to be non-migratable, these materials are selected from the group consisting of: gold, gold alloy, platinum, gold-filled-thermal-setting conductive material, platinum-filled-thermal-setting conductive material, gold-bearing glass frit, TiCuSil, CuSil, and gold-based braze.

Referring once again to FIG. 9, one can see that the present invention satisfies all the need for long term human implant. The header block itself 38 is not considered by biomedical scientists to be a long term or reliable hermetic seal. Over time, through bulk permeability, body fluids and water will penetrate readily through that entire structure. This is why there is a hermetic seal to make sure that body fluids can never penetrate to the sensitive electronic circuits of an AIMD, as further explained by U.S. application Ser. No. 11/307,145, the contents of which are incorporated herein. The same principle applies in the present invention, in that, the sensitive microelectronic RFID chip and its associated electrical connections must also be protected over the long term from body fluid intrusion. There are two reasons why this is very important. First of all, moisture intrusion to the level of the RFID chip will cause its sensitive components to short out through formation of metal dendrites or the like. In addition, the electronic RFID chip contains materials that are not biocompatible. They may even contain dangerous toxic materials to the human body, such as lead, cadmium and the like. Accordingly, hermetically sealing the RFID chip is essential.

Figure 11:
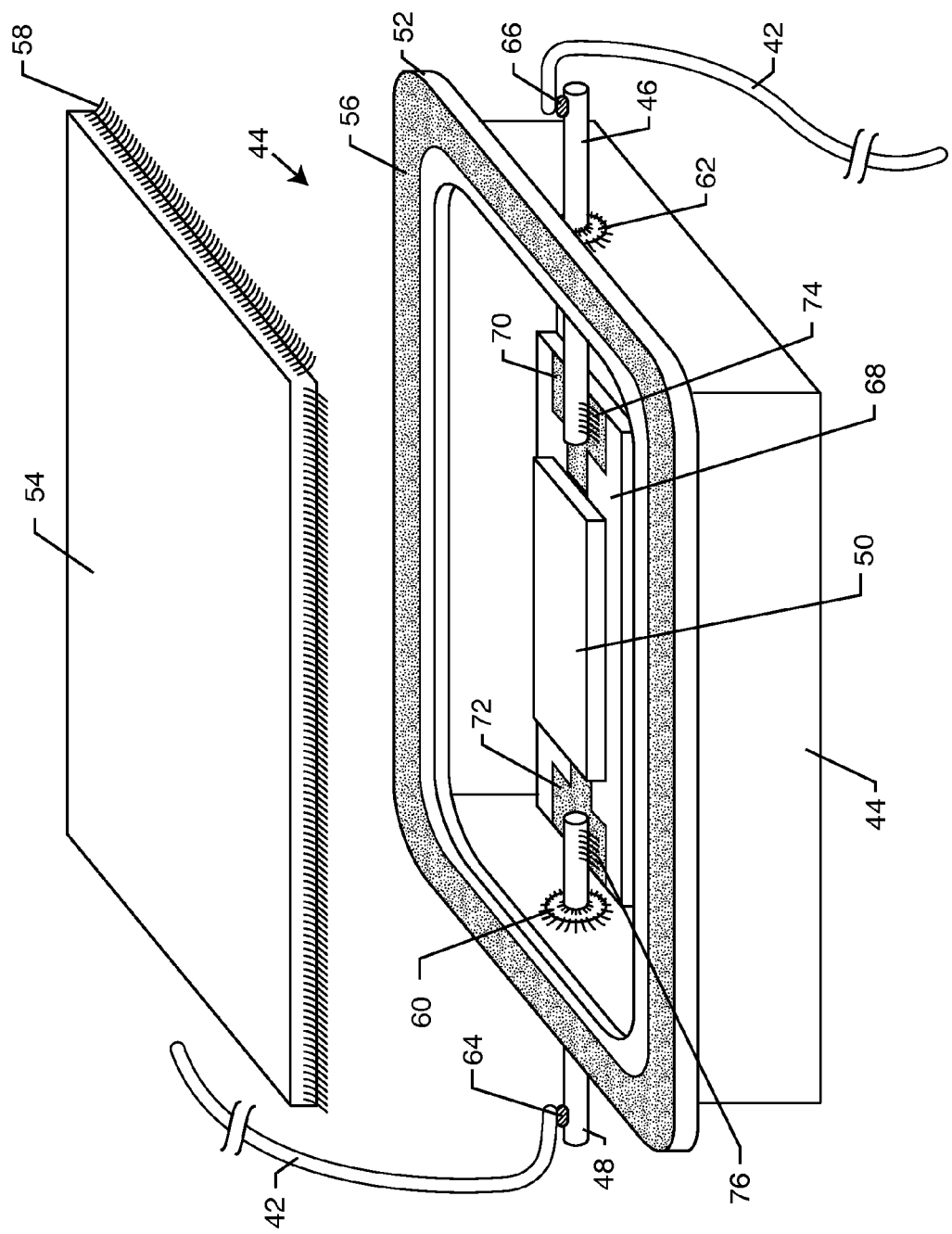
FIG. 11 is an exploded perspective view of the hermetic housing for the RFID chip illustrated in FIG. 10.

FIG. 11 shows an RFID chip 50 inside the hermetically sealed housing 44. The housing can be ceramic with a weld ring 52 and a ceramic lid 54 with a sputtered surface 56 as shown. These weld rings would typically be titanium or platinum and they would be gold brazed 58 to the sputtered ceramic material 56. However, in a preferred embodiment, the entire housing 44 can simply be machined or made from powder metallurgy of titanium so that the entire structure is metal. Through this would penetrate hermetic seals 60 and 62 on each end. These hermetic seals, in a preferred embodiment, would be gold brazed ceramic seals. However, they could also be either fusion or glass compression seals. The terminal pins 46 and 48 extend out either end for convenient welding of the antenna 42 lead at locations 64 and 66 (the antenna itself is not shown). This is typically done by laser welding so that it would be entirely biocompatible. As previously mentioned, this could also be done with a biocompatible thermal-setting conductive adhesive. The RFID chip 50 may be attached to the container 44 by means of a non-conductive substrate 68. Wire bond pads or metallizations 70 and 72 are formed on the substrate 68 and in conductive relation to the RFID chip 50 and the terminal pins 46 and 48, such as by gold braze or laser welds 74 and 76, as shown in FIG. 11. Since these electrical connections 74 and 76 will not be exposed to body fluids, they could also be comprised of solder or any other well-known non-biocompatible material. Referring once again to FIG. 11, electrical connections 64 and 66 can be eliminated. This would be accomplished by using a suitable biocompatible antenna wire 42, such as platinum or platinum-iridium. One could take a setter, which would be typically of zirconia into which ceramic powder could be placed, which would roughly have the shape of housing 44. The antenna lead wire 42 could be of pure platinum or platinum-iridium, which is a high temperature material. The antenna could be laid through the powder in the same position for pins 46 and 48 are presently shown. This entire structure could be co-fired (sintered) such that a platinum antenna lead forms its own hermetic seal into the housing 44. All that would be needed then is to do the lid attachment.

Figure 12:
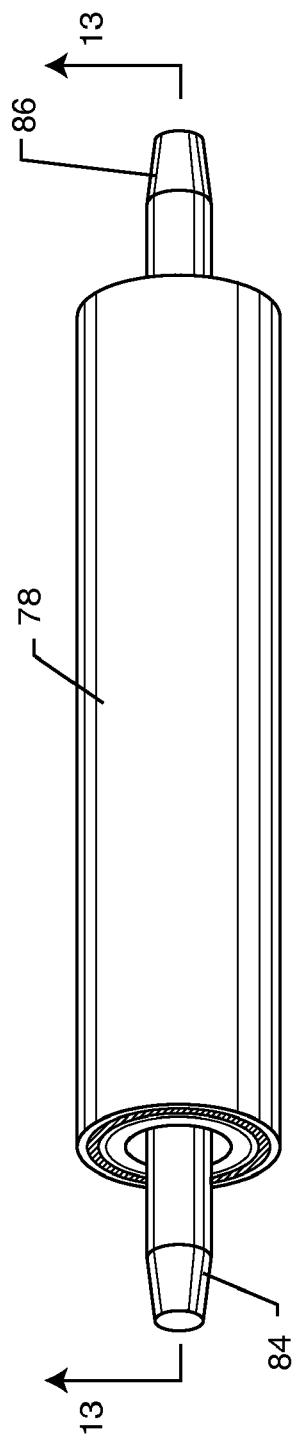
FIG. 12 is a perspective view of an alternative cylindrical hermetic seal utilized to house the RFID microchip.
Figure 13:
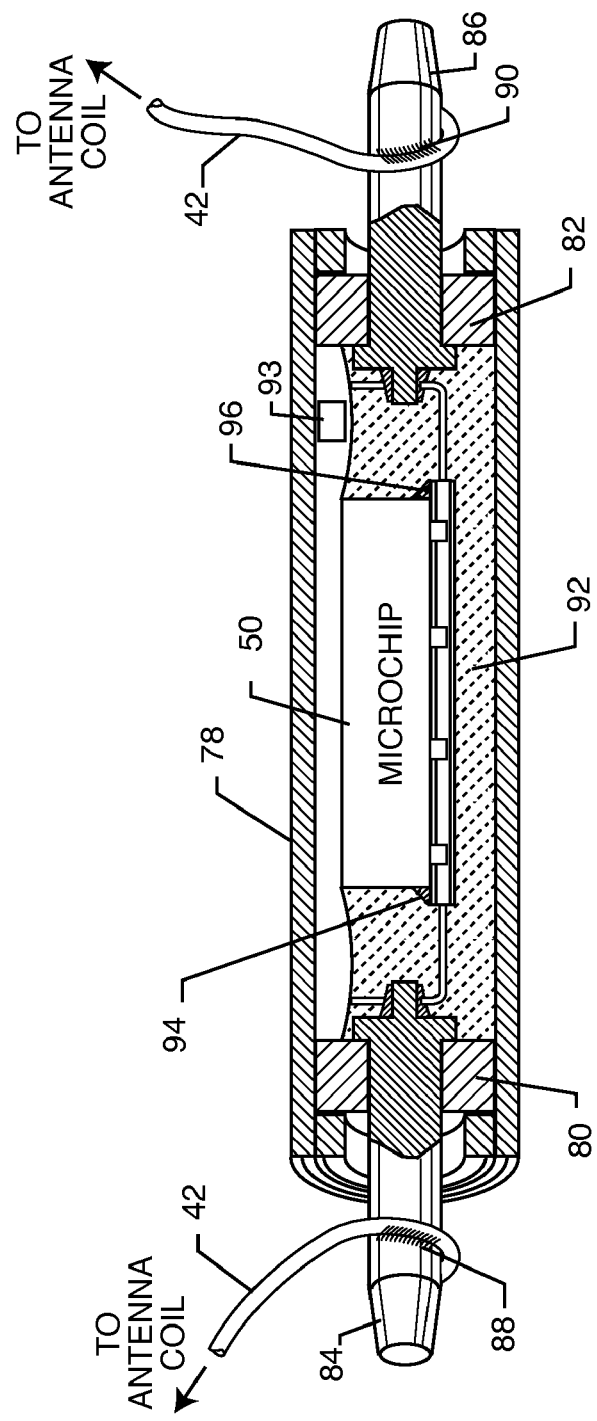
FIG. 13 is a sectional view taken generally along the line 13-13 from FIG. 12.

FIG. 12 is an alternative cylindrical hermetic seal to house the RFID microchip which is very similar to the concept previously described in FIG. 11. FIG. 13 is a sectional view taken from 13-13 from FIG. 12. Shown is an RFID microchip 50 within the hermetic container 78. On either end are hermetic seals 80 and 82 as shown. There are two pins 84 and 86 extending on either side. These pins are electrically isolated from the overall hermetic housing 78. It is important that all of the material as shown in FIG. 12 that could possibly be exposed to body fluids be both non-toxic and biocompatible. In a preferred embodiment, the housing 78 would be of either titanium or platinum. The pins 84 and 86 could also be platinum or similar noble material. The hermetic seal 80 and 82 could be gold brazed alumina seals as is commonly used in AIMDs or it could include compression or fusion glass seals. Electrical connections 88 and 90 are formed between the ends of the antenna coil 42 and both pins 84 and 86. The electrical connection 88 and 90 can be by laser welding or suitable biocompatible thermal-setting conductive adhesives, gold brazes or the like.

Referring once again to FIG. 13, we can see that the microchip 50 has an optional encapsulant 92. This can be any type of non-conductive epoxy, silicone or the like. Since it's inside the hermetic seal, it is not important that this material be non-toxic or biocompatible. There is also an optional desiccant 93 within the housing 78. There are also electrical connections 94 and 96 which are typically solder joints which connect to the RFID chip 50 to pins 84 and 86. There are also a number of other connections on the microchip. If one were to look at a high magnification photograph of a microchip, one would see that there are literally hundreds or even thousands of miniature electrical connections. The materials in the electrical connections of the microchip itself are generally not biocompatible and can be toxic to body tissue. This is another important reason why both the microchip and all of its associated electrical components and connections must be housed inside a non-toxic hermetically sealed biocompatible container. Hermetic, in this context, does not mean a glass tube is back-filled with silicone or epoxy or the header block of an AIMD, which is generally a polymer or even most glass seals. Over long periods of time, through bulk permeability, it has been demonstrated that moisture can penetrate such structures. In general, the term hermetic as used herein means a leak rate of not more than $1 \times 10^{-7}$ cc per second. Referring once again to material 92, its purpose is to simply provide mechanical stability for the microchip 50 so that it is resistant to shock and vibration or movement within the human body. As previously mentioned, when attached to the multi-turn RFID loop antenna 42, the entire structure consisting of fine wire is relatively flexible. This is important if this were to be installed in a way that is not associated with an AIMD.

Figure 14:
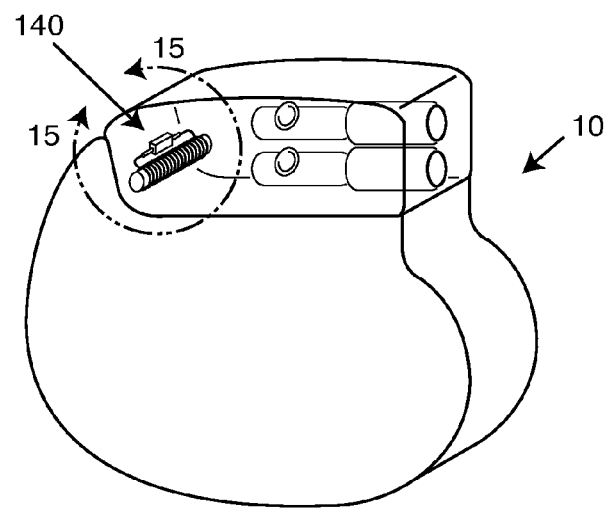
FIG. 14 is a perspective view of an AIMD having an RFID tag embodying the present invention embedded in a header block thereof.

FIG. 14 represents a prior art AIMD 10, such as a cardiac pacemaker that was previously illustrated in FIGS. 8 and 9. Referring to FIG. 14, one can see that there is a novel RFID chip and antenna 140 of the present invention. The RFID tag 140 includes a hermetically sealed RFID chip 144 and external antenna 142. In this case, the external antenna 142 is a solenoid style antenna, which may be optionally wound around a ferrite core 146. Solenoid type RFID antennas are well known in the prior art. U.S. Pat. No. 7,443,362, the contents of which are incorporated herein by reference, describes a number of novel solenoid antenna designs for use in conjunction with RFID systems, badge readers, proximity sensors and short-range data lengths.

Figure 15:
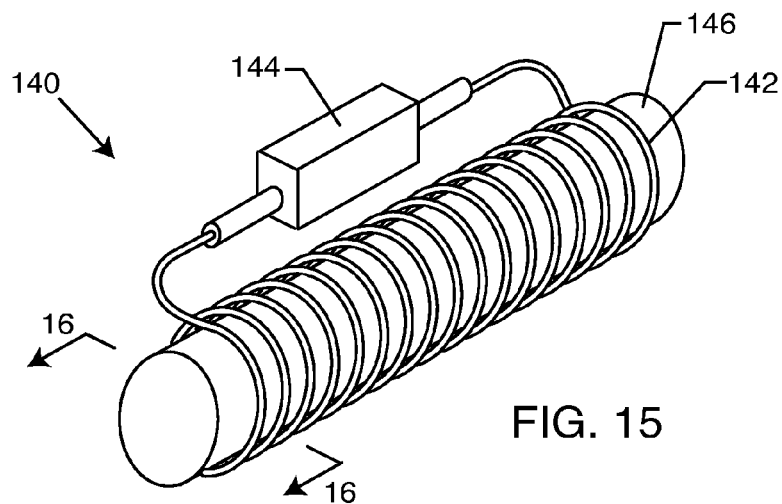
FIG. 15 is an enlarged perspective view of an RFID tag structure embodying the present invention and taken generally of the area designated by line 15-15 of FIG. 14.

FIG. 15 is a blown-up view taken generally from section 15-15 from FIG. 14. Referring to FIG. 15, one can see that the hermetically sealed RFID microelectronic chip 144 is the same package that was previously illustrated in FIG. 11. Also, shown in FIG. 15 is the external antenna 142 which consists of multiple turns of biocompatible wire in a solenoid-type configuration. Also shown is the optional ferrite core 146, which has an optional biocompatible coating 148.

Figure 16:
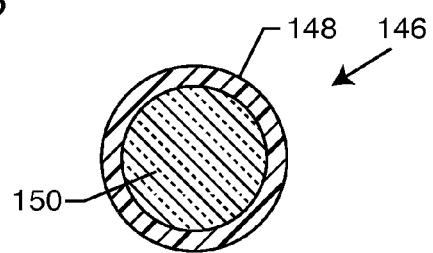
FIG. 16 is a cross-sectional view taken generally along line 16-16 of FIG. 15.

FIG. 16 is a sectional view of the ferrite core 146 taken generally from section 16-16 from FIG. 15. Referring to FIG. 16, one can see that the ferrite core 146 consists of a high temperature sintered ferrite material 150. This is important because it reaches a ceramic-type state wherein the magnetic dipoles are tightly bound up within the ceramic matrix. This is important for biocompatibility so that toxic ferromagnetic materials, such as nickel alloys, do not leach out. Also shown is an optional biocompatible conformal coating 148 which assists in the biocompatibility of the ferrite core 150. In general, the coating 148 consists of a dielectric material which can include the biocompatible dielectric material which can include parylene, ETFE, PTFE, polyimide, polyurethane, silicone or the like.

Referring once again to FIGS. 14-16, it is important to implant applications for humans that the ferrite material 150 of the core 146 be carefully chosen. This has to do with the fact that the human, may at some point in their lives, undergo a medical diagnostic procedure known as magnetic resonance imaging (MRI). MRI equipment embodies three main fields, one of which is known as the $B_0$ main static field. The main static field of an MRI scanner is more than a hundred thousand times more powerful that the earth's magnetic field. This tends to align magnetic domains of a ferromagnetic material. Since it is not important that the RFID tag be read during an actual MRI scan, then it is not particularly important that the ferrite material 150 be saturated during an MRI scan. In the saturated condition, the external antenna 142 as illustrated in FIG. 15 would become highly inefficient. What this means is it would not be possible to interrogate the RFID tag 140 while the patient was in the presence of a main static field of an MRI scanner. However, this would require that the patient be inside the bore at which time there is really no need that the tag be operable. What is important in the present invention is that the magnetic ferrite material 150 that is used be carefully selected such that it not be permanently damaged by exposure to the MR main static field. Certain ferrite materials, when exposed to a powerful magnetic field, will have their magnetic dipoles aligned. After removal of the powerful magnetic field, those dipoles will remain aligned in a condition known as magnetic remanence. This is a form of magnetic memory which would be very detrimental. If the ferrite material remained in a remnant condition, this would mean that the tag would be ruined and would no longer be capable of being read after the MRI scan. Accordingly, it is a property of the present invention that the selection of the ferrite be done generally using soft ferrites or other ferrite material that will not exhibit permanent remanence after exposure to MRI.

It is also a feature of the present invention that the entire non-toxic biocompatible RFID tag system 40 as shown FIGS. 10-13 could be molded or embedded in a thin medical grade plastic disk. This could be a thin silicone disk, a thin epoxy disk or a thin polyimide disk. With a suitable adhesive, this would allow it to be attached to, for example, the housing or header block of an AIMD, such as a cardiac pacemaker or even a hip implant. It could also be implanted through a small incision in various other locations in the body, or it could even be injected with a large needle syringe.

The novel biocompatible antenna and hermetically sealed RFID chip of the present invention, such as illustrated in FIGS. 10-13, does not need to be associated with a pacemaker or other type of AIMD. The RFID chip 50 and associated biocompatible and non-toxic antenna 42 could be implanted in accordance with FIG. 3 in the abdominal 100, into the arm 102 or even the buttocks 114. Since these areas are all subject to some movement, flexibility of the antenna structure 42, as illustrated in FIG. 11, is important. The antenna structure and hermetically sealed RFID chip 50 could be over-molded with silicone or other thin biocompatible, but flexible material. Flexibility of the entire structure is important because no matter where you implant this in the human body, it is subject to some motion. The arm would be an extreme example where motion could occur. The novel hermetically sealed RFID chip and associated non-toxic and biocompatible antenna 40 of the present invention need not be only for identification from a medical implant. It could also be used generally for human identification. This would include prior art applications where lights in a building could be turned on and off automatically as the implanted RFID chip 50 is sensed, doors could be opened and the like. The RFID chip 50 could also contain encrypted information such as Social Security No., credit card information and the like. This would facilitate automated checkout from retail stores and the like.

Figure 17:
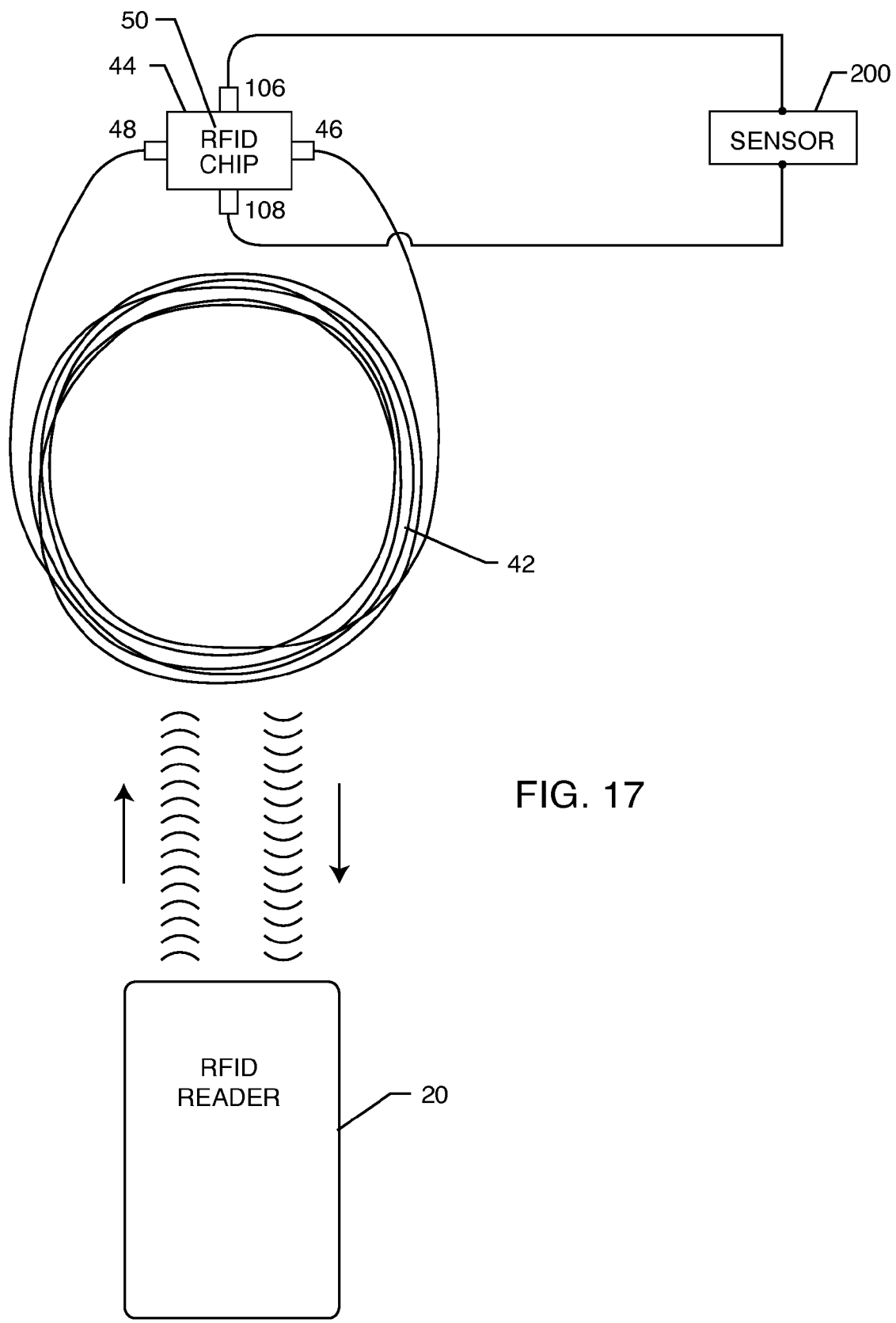
FIG. 17 is a block diagram illustrating a system of an RFID reader communicating with a hermetically sealed RFID chip which is associated with a biocompatible antenna.

FIG. 17 is a block diagram showing a system of an RFID reader 20 that is communicating with a hermetically sealed RFID chip 44 associated with a biocompatible antenna 42 of the present invention. The RFID chip 50 (not shown) is enclosed within the hermetic housing 44 which is very similar to the hermetic housing that was previously described in FIG. 11. However, close examination of the hermetic housing shows that it has four terminals instead of two, as was previously illustrated in FIG. 11. The other two terminals 106 and 108 are connected to an external sensor 200. The sensor can be a variety of sensors 200 to transmit important information about activities within the human body. For example, this could be a motion sensor, an accelerometer, a pressure transducer, for example, to measure pressures within a cardiac chamber, motion sensors to measure cardiac ventricular wall motion, blood gas sensors and the like. When interrogated, the RFID chip 50 would take information from the sensor and transmit it to the RFID reader 200. In this way, medical personnel could, in real time, gain important information about the patient. For example, if the patient had a heart valve replacement, the RFID chip 50 and sensor 200 could be associated with said valve. The RFID chip 50 could transmit important information about the proper operation of the prosthetic heart valve leaflets.

Figure 18:
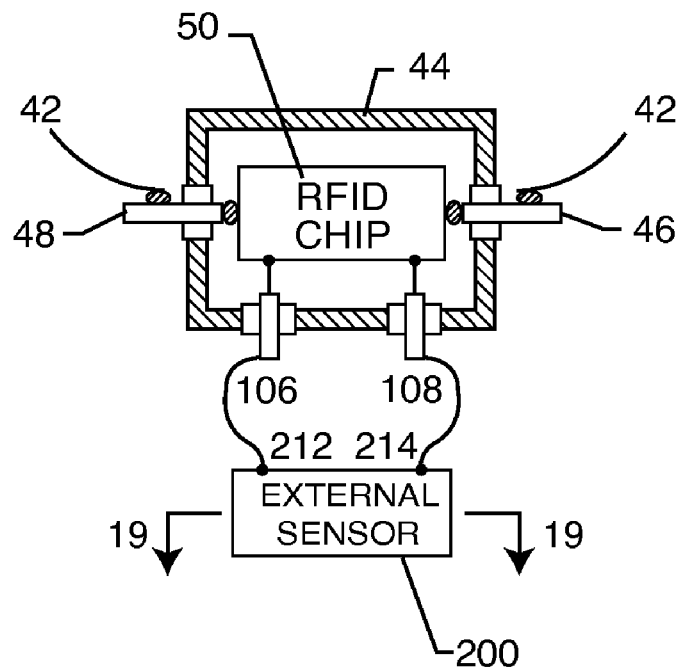
FIG. 18 illustrates the RFID chip is in its own hermetic package and wired to an external sensor.
Figure 19:
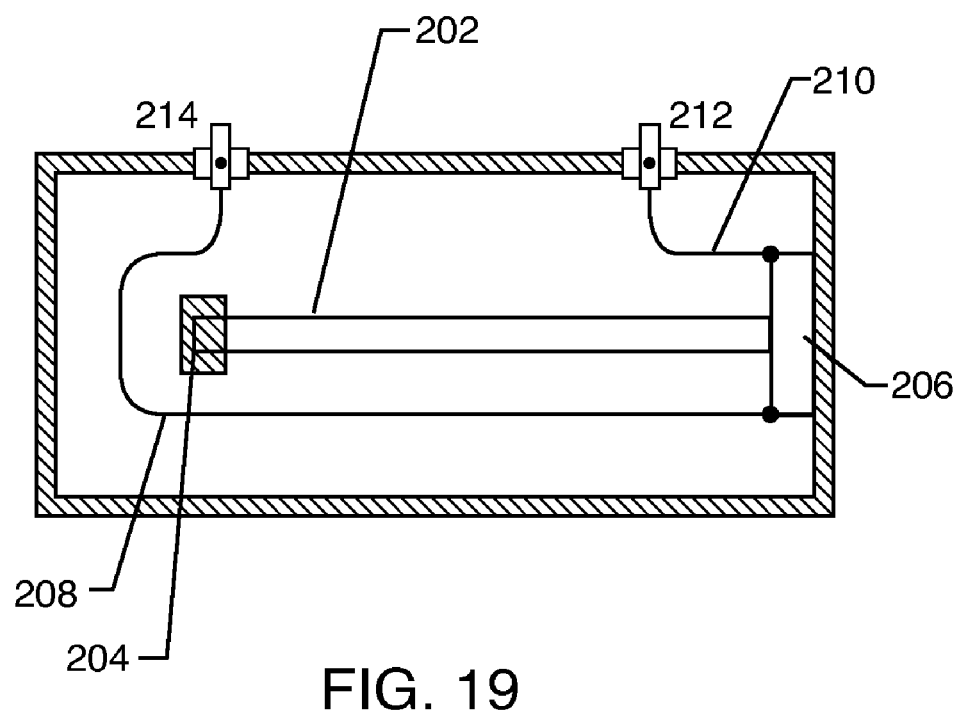
FIG. 19 is a sectional view of the external sensor shown in FIG. 18.

FIG. 18 is very similar to FIG. 17 with the RFID chip 50 in its own hermetic package 44 and wired through terminal pins 46 and 48 to an external biocompatible antenna 42. An external sensor 200 is wired to the RFID chip 50 through terminal pins 106 and 108. FIG. 19 is a sectional view taken from section 19-19 of a typical external sensor 200 as previously illustrated in FIG. 18. Referring once again to FIG. 19, in this case, one can see that this is a motion sensor. In this case, there is a piezoelectric cantilever arm 202 with a weight 204 attached to its end. With motion, the cantilever beam 202 deflects or oscillates and generates electricity through piezoelectric action. The cantilever arm 202 is connected to a base 206 and lead wires 208 and 210 are routed to terminal pins 212 and 214. As previously described, the present invention is not limited to just motion sensors, but is applicable to a wide range of sensors, relays, transducers or actuators as may be implanted within a human body. As used herein, the term human body is inclusive to include all vertebrates and all animals. In other words, the present invention is not limited to just humans.

Figure 20:
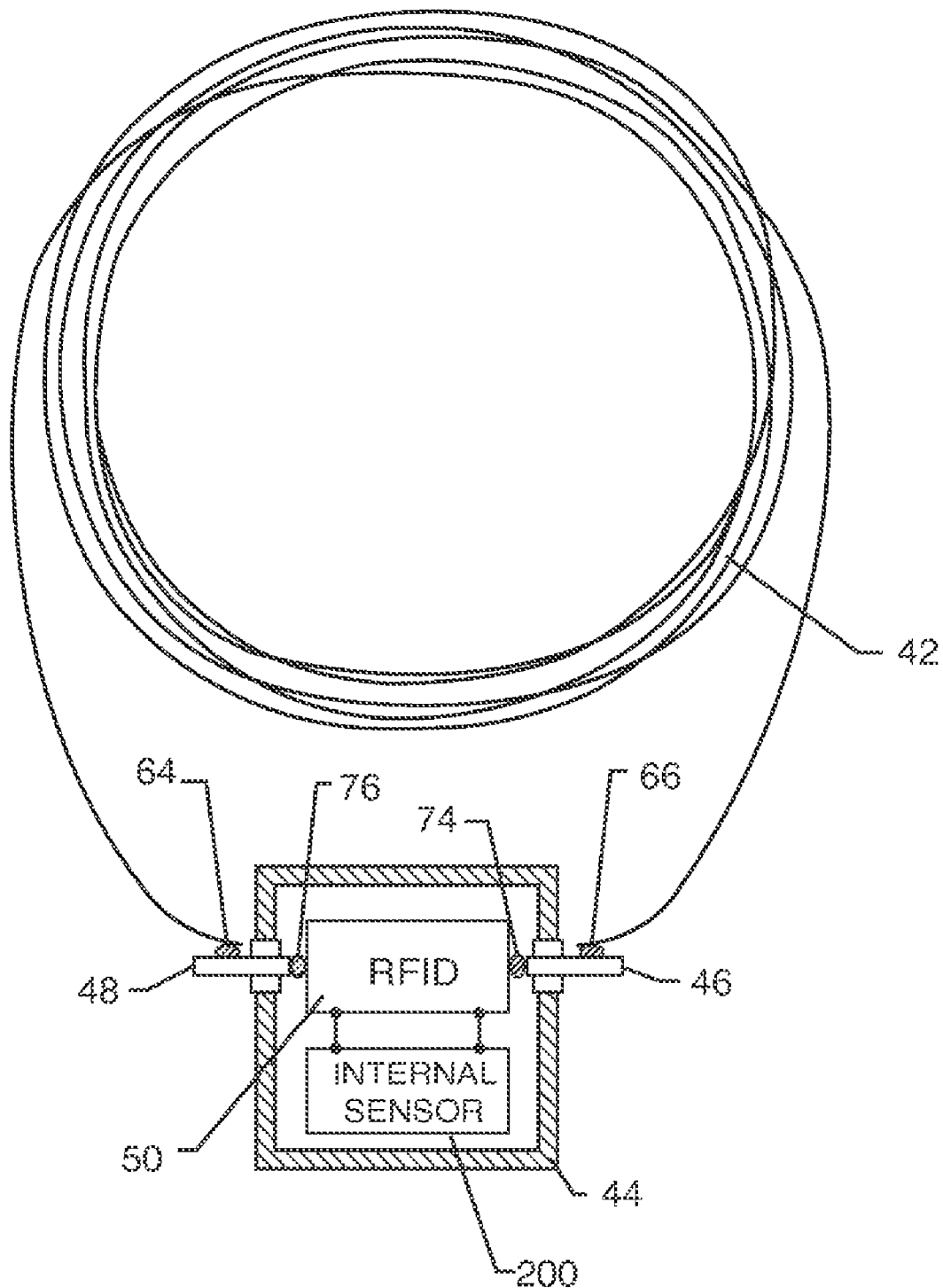
FIG. 20 is a view similar to FIG. 18, with the exception that the RFID chip is connected to an internal sensor.

FIG. 20 is a close-up view of a hermetically sealed housing 44 similar to FIG. 18 except that the RFID chip 50 is connected to an internal sensor 200.

From the foregoing it will be appreciated that a novel aspect of the present invention resides in providing a relatively large non-hermetically sealed biocompatible multi-turn RFID loop antenna 42 which is electrically connected to a miniature RFID chip 50 that is enclosed within its own hermetically sealed miniature container 44. The hermetic seal can be very small and the loop antenna can be relatively large wherein the entire package is both highly reliable, resistant to body fluids and completely biocompatible. Such structure is adaptable for being molded into the header block, for example, for a cardiac pacemaker or, alternatively it can be put in an optimal small silicone disk and implanted directly in the human body.

As used herein, medical implant includes all active implantable medical devices, such as cardiac pacemakers, implantable cardioverter defibrillators (ICDs), neurostimulators and the like. The present invention also applies to all types of passive implants, including heart valves, hip replacements, stents and the like. In fact, the present invention does not actually have to be associated with implanted medical devices at all. It could be implanted in a human and used for other purposes, such as opening doors, turning on lights in a building, etc.

It is a feature of the present invention that the novel hermetically sealed RFID chip with fixation device can be used to attach to one or more abandoned leads in the pectoral pocket. This is very useful whether or not the patient receives a new pacemaker or AIMD, implant or not. That is, if we have a patient that has reverted to normal sinus rhythm and no longer needs a pacemaker and has abandoned leads, the radiology department can quickly tell through the RFID scan whether or not abandoned lead wires are present. As mentioned, this is extremely important to prevent inadvertent MRI on such a patient. In the past, it has been shown that abandoned leads can heat up so much that ablation of cardiac tissue and even perforation of cardiac walls can occur. It is, therefore, a feature of the present invention that both the lead wire system and the AIMD can be separately identified.

Although several embodiments have been described in detail for purposes of illustration, various modifications may be made without departing from the scope and spirit of the invention. Accordingly, the invention is not to be limited, except as by the appended claims.

What is claimed is:

1. An implantable medical device comprising:
    a) hermetically sealed biocompatible housing;
    b) an RFID microelectronics chip disposed within the housing;
    c) an antenna wire having a first end portion electrically connected to a first end of the RFID chip inside the housing and extending along a length to a second end portion electronically connected to a second end of the RFID chip inside the housing with at least an intermediate portion of the length of the antenna wire between the first and second end portions residing outside the housing; and
    d) a sealing material that hermetically seals against an outer surface of the first and second end portions of the antenna wire and against respective perimeter openings in the housing through which the antenna wire extends, wherein the intermediate portion of the antenna wire external to the housing serves as an antenna for the RFID microelectronics chip.

2. The implantable medical device of claim 1, wherein the housing has a leak rate of no more than $10^{-7}$ centimeters per second.

3. The implantable medical device of claim 2, wherein the housing is of a material selected from the group consisting of biocompatible metals and alloys, ceramic, glass, porcelain, sapphire and composites thereof, and specialty polymer composites.

4. The implantable medical device of claim 3, including a desiccant within the housing.

5. The implantable medical device of claim 3, including an encapsulant within the housing surrounding at least a portion of the RFID chip.

6. The implantable medical device of claim 5, wherein the encapsulant is comprised of a thermal-setting polymer or a silicone material.

7. The implantable medical device of claim 1, wherein the housing includes a cap hermetically sealed to an open end of a housing container.

8. The implantable medical device of claim 1, wherein the RFID chip is read-only or readable/writable.

9. The implantable medical device of claim 1, wherein the RFID chip is communicable with an external device at a radio frequency of from 125 kHz to 915 MHz.

10. The implantable medical device of claim 9, wherein the RFID chip is communicable with an external device at a radio frequency of approximately 13.56 MHz.

11. The implantable medical device of claim 1, wherein the RFID chip includes information relating to a patient in which the medical device is implanted.

12. The implantable medical device of claim 1, wherein the container, RFID chip, and at least the first and second end portions of the antenna wire are embedded within a non-conductive biocompatible material.

13. The implantable medical device of claim 12, wherein the biocompatible material comprises a disc of a material selected from the group consisting of silicone, epoxy, and a medical grade plastic.

14. The implantable medical device of claim 1, wherein the intermediate portion of the antenna wire is wound around a ferrite-based core.

15. The implantable medical device of claim 14, wherein the ferrite-based core comprises a high temperature sintered ferrite-based material.

16. The implantable medical device of claim 15, including a biocompatible dielectric material at least partially coating the ferrite-based material.

17. The implantable medical device of claim 16, wherein the biocompatible dielectric material is selected from the group consisting of parylene, ETFE, PTFE, polyimide, polyurethane, and silicone.

18. The implantable medical device of claim 14, wherein the ferrite-based core is comprised of a ferrite material that will not exhibit permanent remanence after exposure to MRI fields.

19. The implantable medical device of claim 1, including a sensor conductively coupled to the RFID microelectronics chip.

20. The implantable medical device of claim 19, wherein the sensor is disposed exterior of the hermetically sealed housing.

21. The implantable medical device of claim 19, wherein the sensor is disposed within the hermetically sealed housing.

22. The implantable medical device of claim 19, wherein the RFID chip is capable of transmitting data measured by the sensor in real time.

23. The implantable medical device of claim 22, wherein the measurable data comprises the activity of a human body.

24. The implantable medical device of claim 1 wherein the intermediate portion of the antenna wire is a multi-turn antenna.

25. The implantable medical device of claim 1 wherein the first and second end portions of the antenna wire are first and second feedthrough wires that are hermetically sealed in the respective openings in the housing and opposed end of the intermediate portion of the antenna wire are electrically connected to the first and second feedthrough wires.

26. The implantable medical device of claim 1 wherein the hermetically sealed housing is the housing for an active implantable medical device.

27. The implantable medical device of claim 1 wherein the hermetically sealed housing s of titanium or stainless steel.

28. An implantable medical device, comprising:
a) a hermetically sealed biocompatible housing;
b) an RFID microelectronics chip disposed within the housing;
c) an antenna wire having a first end portion electrically connected to a first end of the RFID chip inside the housing and extending along a length to a second end portion electronically connected to a second end of the RFID chip inside the housing with at least an intermediate portion of the length of the antenna wire between the first and second end portions residing outside the housing; and
d) wherein a wall of the housing hermetically seals against an outer surface of the first and second end portions of the antenna wire, wherein the intermediate portion of the antenna wire external to the housing serves as an antenna for the RFID microelectronics chip.

29. An implantable medical device, comprising:
a) a hermetically sealed biocompatible housing;
b) an RFID microelectronics chip disposed within the housing;
c) a first feedthrough wire comprising a first proximal end electrically connected to the RFID chip and a first distal end residing outside the hermetically sealed housing, wherein a first sealing material hermetically seals against an outer surface of the first feedthrough wire and against a first perimeter opening in the housing through which the first feedthrough wire extends;
d) a second feedthrough wire comprising a second proximal end electrically connected to the RFID chip and a second distal end residing outside the hermetically sealed housing, wherein a second sealing material hermetically seals against an outer surface of the second feedthrough wire and against a second perimeter opening in the housing through which the second feedthrough wire extends; and
e) an antenna wire having a first end electrically connected to the first distal end of the first feedthrough wire outside the housing and extending along a length to a second end electronically connected to the second distal end of the second feedthrough wire outside the housing.

30. A medical system comprising:
a) an implantable medical device;
b) a hermetically sealed biocompatible housing that is either contained inside the implantable medical device or contacted to an outer surface thereof;
c) an RFID microelectronics chip disposed within the housing;
d) an antenna wire having a first end portion electrically connected to a first end of the RFID chip inside the housing and extending along a length to a second end portion electronically connected to a second end of the RFID chip inside the housing with at least an intermediate portion of the length of the antenna wire between the first and second end portions residing outside the housing; and
e) a sealing material that hermetically seals against an outer surface of the first and second end portions of the antenna wire and against respective perimeter openings in the housing through which the antenna wire extends, wherein the intermediate portion of the antenna wire external to the housing serves as an antenna for the RFID microelectronics chip.

31. The system of claim 3 including an interrogator for electromagnetically communicating with the RFID chip.

32. The system of claim 31 wherein the interrogator is a read only or a reader/writer device.

33. The system of claim 31 wherein the interrogator is capable of communicating with a computer or a computer network.

34. The system of claim 30 wherein the hermetically sealed housing for the RFID chip is disposed within a non hermetically sealed portion of the medical device.

35. The system of claim 30 wherein the hermetically sealed housing for the RFID chip is disposed within a header block of the medical device.

36. The system of claim 30 wherein the antenna wire and the RFID chip are disposed within the medical device parallel to a length and height plane of the medical device, and midway through the width thereof.

37. The system of claim 30 wherein the RFID chip includes information pertaining to the medical device.

38. The system of claim 30 wherein the implantable medical device is selected from the group consisting of a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, a Bion or a prosthetic device, and component parts thereof, including lead wires and abandoned lead wire.

* * * * *

UNITED STATES PATENT AND TRADEMARK OFFICE
CERTIFICATE OF CORRECTION

| | | |
|---|---|---|
| PATENT NO. | : 8,253,555 B2 | |
| APPLICATION NO. | : 12/566223 | |
| DATED | : August 28, 2012 | |
| INVENTOR(S) | : Stevenson et al. | |

It is certified that error appears in the above-identified patent and that said Letters Patent is hereby corrected as shown below:

In the Claims:

Column 16, line 15 insert the word --cubic-- after the word centimeters

Signed and Sealed this
Twenty-first Day of May, 2013

Teresa Stanek Rea
*Acting Director of the United States Patent and Trademark Office*